United States Patent [19]
Yoshida et al.

[11] Patent Number: 6,086,874
[45] Date of Patent: Jul. 11, 2000

[54] ANTITUMOR AGENT EFFECT ENHANCER CONTAINING IL-6 ANTAGONIST

[75] Inventors: Osamu Yoshida; Youichi Mizutani, both of Kyoto, Japan

[73] Assignee: Chugai Seiyaku Kabushiki Kaisha, Tokyo, Japan

[21] Appl. No.: 08/860,487

[22] PCT Filed: Dec. 28, 1995

[86] PCT No.: PCT/JP95/02769

§ 371 Date: Jun. 27, 1997

§ 102(e) Date: Jun. 27, 1997

[87] PCT Pub. No.: WO96/20728

PCT Pub. Date: Jul. 11, 1996

[30] Foreign Application Priority Data

Dec. 29, 1994 [JP] Japan .................................. 6-340425

[51] Int. Cl.$^7$ ........................ A61K 39/395; C07K 16/24; C12P 21/08; C09K 16/28
[52] U.S. Cl. .................................. 424/133.1; 424/138.1; 424/141.1; 424/143.1; 424/144.1; 424/145.1; 424/152.1; 424/155.1; 424/158.1; 424/172.1; 424/174.1; 530/387.1; 530/387.3; 530/388.22
[58] Field of Search ............................ 424/133.1, 143.1, 424/155.1, 141.1, 144.1, 145.1, 138.1, 152.1, 158.1, 172.1, 174.1; 530/387.1, 387.3, 387.7, 388.22

[56] References Cited

FOREIGN PATENT DOCUMENTS 9220364  11/1992  WIPO .

OTHER PUBLICATIONS

Emilie et al. Blood, vol. 84, No. 8 (Oct. 15) 1994 pp. 2472–2479.
Masayuki et al 1993 Cancer Res 53:851–856.
Aapro et al 1983 Cancer Chemother. Pharmacol. 10(3):161–166—Abstract Only.
Cancer (4$^{th}$ ed) Devita et al Eds. Lippincott Co, Philadelphia, 1993.
Shepard et al., J. of Clinical Immunology vol. 11, No. 3 pp. 117–127, 1991.
Mizutani et al., "Sensitization Of Human Renal Cell Carcinoma Cells To cis–Diamminedichloroplatinum (II) By Anti–Interleukin 6 Monoclonal Antibody Or Anti–Interleukin 6 Receptor Monoclonal Antibody", Cancer Research, Feb. 1, 1995, vol. 55, pp. 590–596.
Mizutani et al., Proceedings Of the American Association For Cancer Research, vol. 36, p. 340, No. 2027, (Mar. 1995).
Mizutani et al., 27th Kyoto Jinzo Men–eki Kenkyukai, Abstract and English trans. (1997).
Mizutani et al., The Journal Of Japan Society For Cancer Therapy, (1995), vol. 8, p. 1270, No. 427.
Vink et al., A Journal of Experimental Medicine, Sep. 1990, vol. 172, No. 3, pp. 997–1000.

Primary Examiner—Geetha P. Bansal
Attorney, Agent, or Firm—Burns, Doane, Swecker & Mathis, L.L.P.

[57] ABSTRACT

The present invention discloses an effect enhancer for antitumor agents, examples of which include platinum compounds such as cisplatin and carboplatin, and mitomycin C, that contains interleukin-6 (IL-6) antagonist, examples of which include antibody to IL-6, antibody to IL-6 receptor, and antibody to gp130 protein.

20 Claims, 10 Drawing Sheets

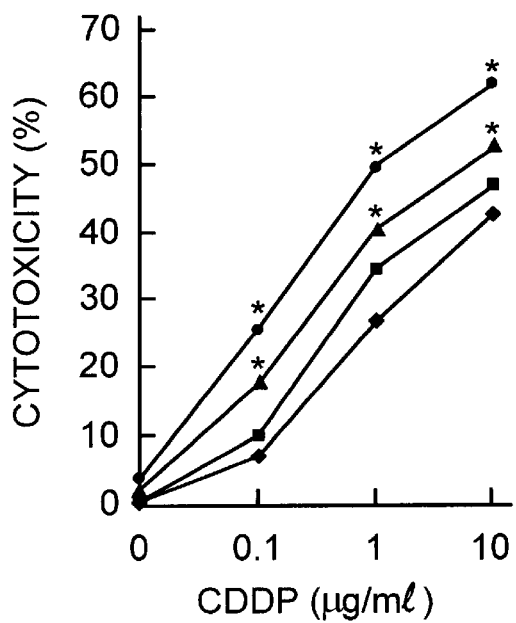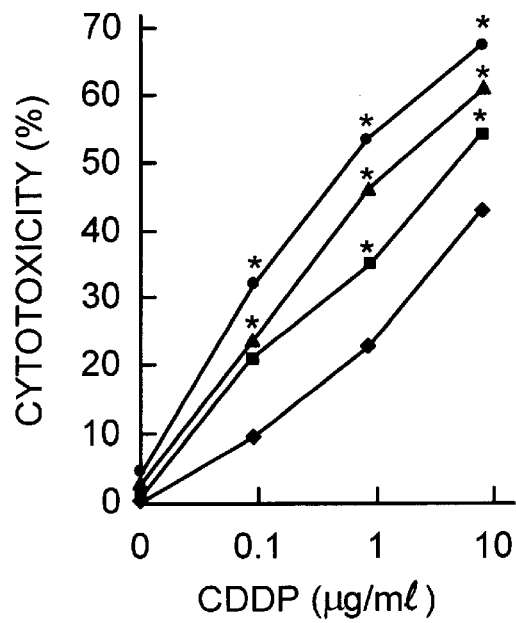
FIG. 1A
ANTI-IL-6
CELLS: CaKi-1
FIG. 1B
ANTI-IL-6R
CELLS: CaKi-1

ANTI-IL-6

CELLS: CaKi-1

ANTI-IL-6R

CELLS: CaKi-1

ANTI-IL-6

CELLS: CaKi-1/DDP

ANTI-IL-6R

CELLS: CaKi-1/DDP

ANTI-IL-6

CELLS: ACNH

ANTI-IL-6R

CELLS: ACNH

FIG. 5A
ANTI-IL-6
FIG. 5B
ANTI-IL-6R
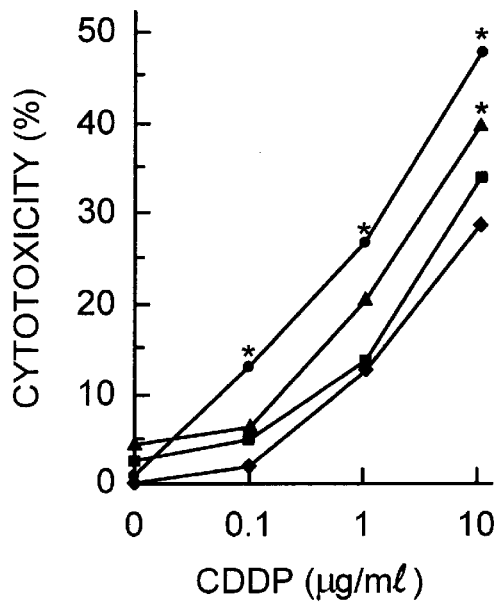
CELLS: A704
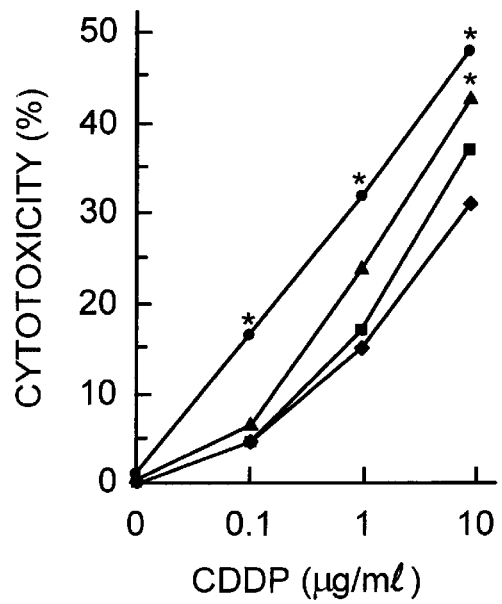
CELLS: A704

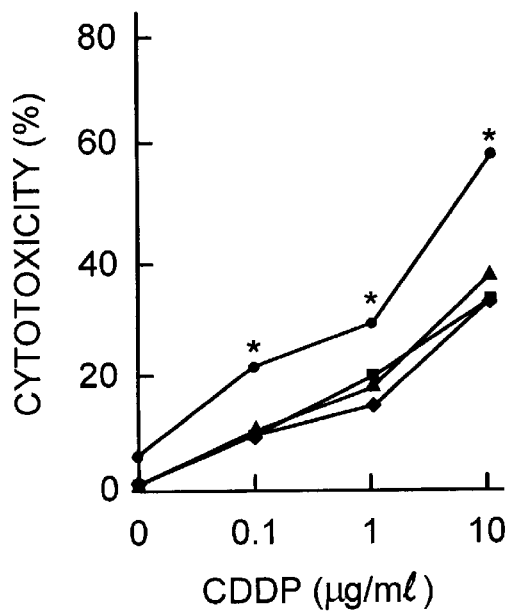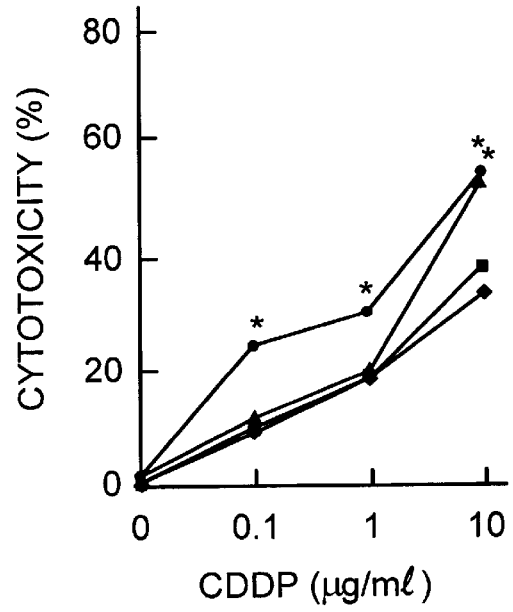

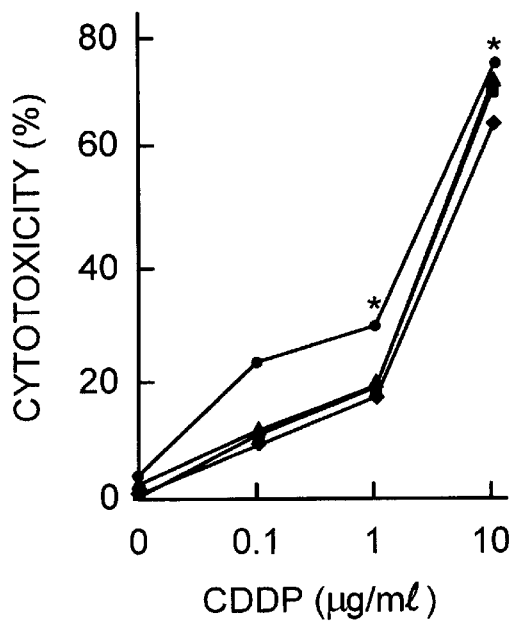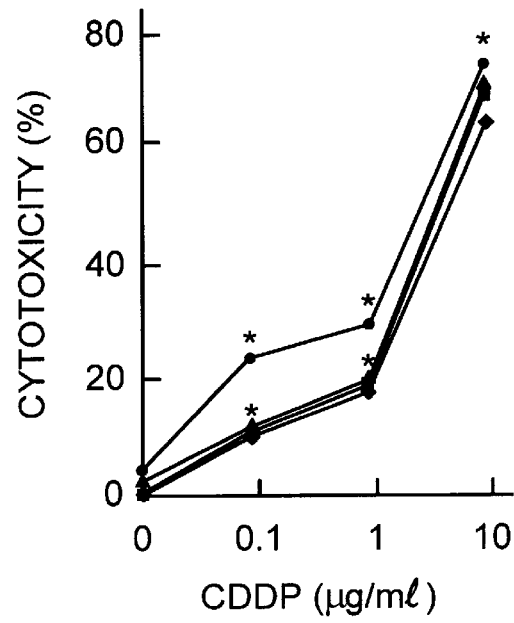

FIG. 8A
ANTI-IL-6
FIG. 8B
ANTI-IL-6R
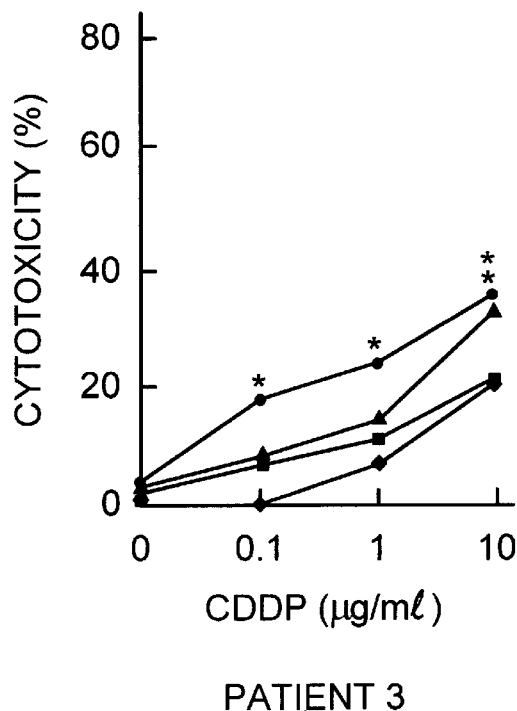
PATIENT 3
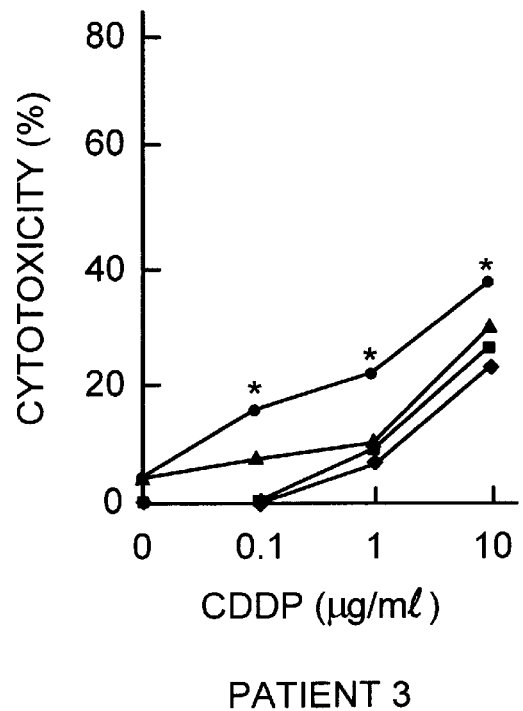
PATIENT 3

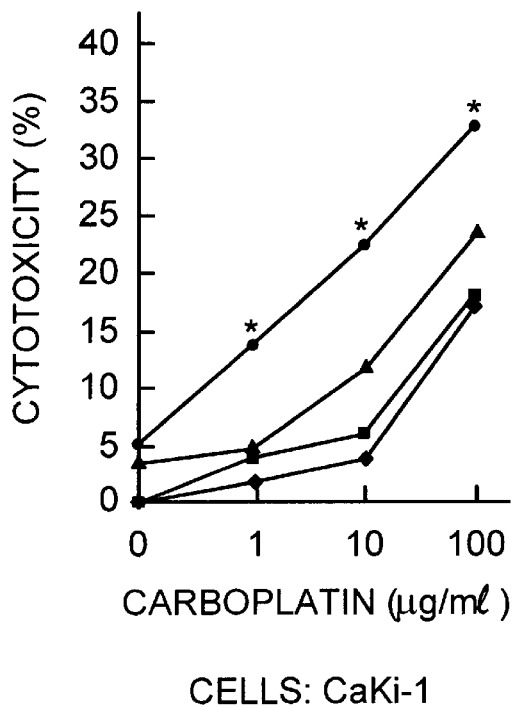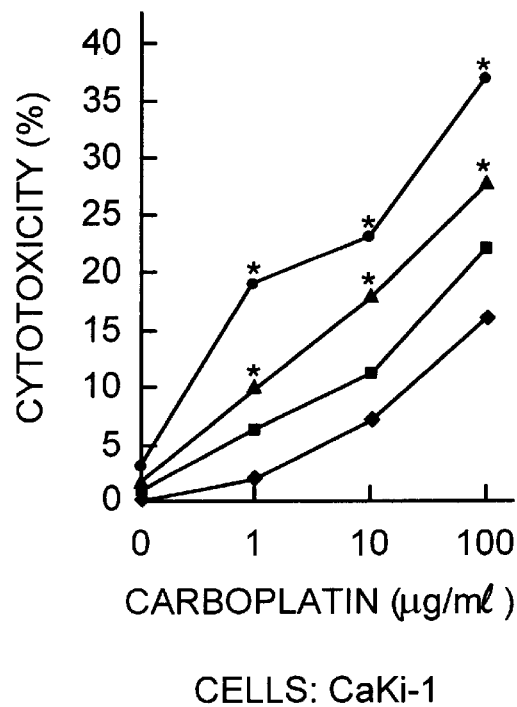
FIG. 9A ANTI-IL-6
CELLS: CaKi-1
FIG. 9B ANTI-IL-6R
CELLS: CaKi-1

ANTITUMOR AGENT EFFECT ENHANCER CONTAINING IL-6 ANTAGONIST

This application is a 371 of PCT/JP95/02769 filed Dec. 28, 1995.

TECHNICAL FIELD

The present invention relates to an antitumor agent effect enhancer comprising interleukin-6 antagonist that assists and enhances the effects of antitumor agents in the treatment of tumors.

BACKGROUND ART

Various drugs such as alkylating agents, metabolism antagonists, antitumor antibiotics and platinum compounds have been used in the past for chemotherapy on human tumors. In the case where remarkable therapeutic effects are not observed when these antitumor agents are used alone, therapeutic methods have been devised in which a plurality of antitumor agents are used concomitantly (Frei, E. III, Cancer Res., 32, 2593–2607, 1992). Tumor cells exhibit various sensitivities to antitumor agents, and certain cells are known to exhibit resistance to therapy by antitumor agents (Magrath, I., New Directions in Cancer Treatment, 1989, Springer-Verlag). Acquisition of resistance to therapy by tumor cells is said to be caused by, for example, the occurrence of multi-drug resistance (MDR) (Tsuruo, T. et al., Cancer Res., 42, 4730–4733, 1982), reduction in cell uptake of antitumor agent (Sherman, S. E. et al., Science, 230, 412, 1985), increased DNA repair activity (Borch, R. F., Metabolism and Action of Anticancer Drugs, Powis, G. & Prough, R. ed., Taylor & Francis, London, 1987, 163–193), or promotion of inactivation of antitumor agent in the cells (Teicher, B. A. et al., Cancer Res., 46, 4379, 1986). In such cases, there are many cases in which the expected therapeutic effects are not observed simply by administering antitumor agent.

Renal cell carcinoma exhibits resistance to therapy to antitumor agents such as cisplatin, adriamycin and vinblastine (Kakehi, Y. et al., J. Urol., 139, 862–864, 1988; Kanamaru, H. et al., J. Natl. Cancer Inst., 81, 844–847, 1989; Teicher, B. A. et al., Cancer Res., 47, 388–393, 1987). Platinum compounds such as cisplatin that possess antitumor effects bond with DNA and inhibit DNA synthesis and cell division (Pinto, A. L. et al., Biochica et Biophysica Acta, 780, 167–180, 1985).

The expression of glutathione-S transferase-$\pi$ (GST-$\pi$), inhibition of the effects of cisplatin caused by an increase in intracellular levels of substances containing sulfidryl groups, increased DNA repair activities, or activation of oncogenes such as c-myc is considered to be involved in the resistance to therapy of renal cell carcinoma to cisplatin (Sklar, M. D. et al., Cancer Res., 51, 2118–2123, 1991; Mizutani, Y. et al., Cancer in press, 1994; Nakagawa, K. et al., Japan J. Cancer Res., 79, 301–305, 1988).

In addition, changes in membrane permeability and transport capabilities in tumor cells are said to cause a decrease in cisplatin uptake within the cells, thus increasing resistance to therapy to cisplatin (Richon, V. et al., Cancer Res., 47, 2056–2061, 1987; Waud, W. R. et al., Cancer Res., 47, 6549–6555, 1987). Glutathione, an example of a substance containing sulfidryl groups that is present in the largest amounts in mammalian animal cells, is reported to inactivate cisplatin in cells, and certain types of tumors have been shown to have higher intracellular glutathione and metallothionein levels (Hromas, R. A. et al., Cancer LETT., 34, 9–13, 1987; Taylor, D. M. et al., Eur. J. Cancer, 12, 249–254, 1976).

Glutathione is a tripeptide thiol. It plays an important role in the inactivation of DNA-bonding substances such as alkylating agents and cisplatin and in the repair of cell damage caused by these. One of the effects of GST-$\pi$ is that it promotes inactivation of antitumor agents by causing antitumor agents like those described above to bond to glutathione.

Since renal cell carcinoma produces interleukin-6 (IL-6) and expresses IL-6 receptor (IL-6R), it has been suggested that IL-6 plays some type of role in the growth activity of renal cell carcinoma (Miki, S. et al. FEBS Lett., 250, 607–610, 1989; Takenawa, J. et al., J. Natl. Cancer. Inst., 83, 1668–1672, 1991). Moreover, it has been reported that the level of IL-6 in the serum increases when the prognosis for treatment of renal cell carcinoma patients is poor (Blay, J. et al., Cancer Res., 52, 3317–3322, 1992; Tsukamoto, T. et al., J. Urol., 148, 1778–1782, 1992). However, a clear correlation between IL-6 and the resistance to therapy of renal cell carcinoma to antitumor agents has not yet been found, and is still unknown.

IL-6 is a multi-functional cytokine referred to as B cell stimulating factor-2 or Interferon $\beta 2$. IL-6 was discovered as a differentiation factor involved in the activation of B lymphoid cells (Hirano, T. et al., Nature, 324, 73–76, 1986). Later, it was clearly shown to be a multi-functional cytokine that affects the functions of various cells (Akira, S. et al., Adv. in Immunology, 54, 1–78, 1993). IL-6 transmits its biological activity by means of two proteins present on cells.

One of them is IL-6R, a ligand bonding protein having a molecular weight of approximately 80 KD to which IL-6 bonds. In addition to the cell bonding form which is expressed on the cell membrane by passing through the cell membrane, it is also present as soluble IL-6R (sIL-6R), which is mainly composed of its extracellular region. Another protein is gp130 having a molecular weight of approximately 130 KD that is involved in signal transmission of non-ligand bonding. IL-6 and IL-6R form an IL-6/IL-6R complex. As a result of then bonding with the other membrane protein gp130, the biological activity of IL-6 is transmitted to the cell (Taga, et al., J. Exp. Med., 196, 967, 1987).

Although platinum compounds like cisplatin and antitumor agents such as mitomycin C induce apoptosis in tumor cells, IL-6 has been reported to inhibit apoptosis induced by antitumor agents (Kerr, J. et al., Cancer, 73, 2013–2026, 1994; Sachs, L. et al., Blood, 82, 15–21, 1993). In addition, antitumor agents like cisplatin and mitomycin C have cytotoxic effects on tumor cells as a result of producing free radicals (Oyanagi, Y. et al., Biochem. Pharmacol., 26, 473–476, 1997; Nakano, H. et al., Biochem. Biophys. Acta., 796, 285–293, 1984). IL-6, however, is known to promote the expression of manganese superoxide dismutase (MnSOD), which has the effect of decomposing free radicals, and IL-6 antibody inhibits the expression of this promoted MnSOD (Ono, M. et al., Biochem. Biophys. Res. Commun., 182, 1100–1107, 1992; Dougall, W. C. et al., Endocrinology, 129, 2376–2384, 1991).

However, none of these reports state that the effects of antitumor agents are enhanced by blocking the biological activity of IL-6. In addition, there are no reports of actually attempting to use an IL-6 antagonist as an effect enhancer of antitumor agents.

Although antitumor agents have been used in the treatment of tumors in the past, since large doses of these drugs produce adverse side effects such as nausea, vomiting, kidney and liver function disorders and inhibition of bone marrow function, there have been cases in which it was dangerous to administer the required dose of antitumor agent for adequately demonstrating antitumor effects. In addition, since there are tumors having resistance to therapy in which chemotherapy using ordinary antitumor agents is not effective, there is a need for an effect enhancer that increases the sensitivity of these tumors to antitumor agents.

The object of the present invention is to provide a novel antitumor agent effect enhancer that assists and enhances the effects of antitumor agents and increases the sensitivity of therapy-resistant tumor cells to antitumor agents. More specifically, the present invention provides an antitumor agent effect enhancer comprising IL-6 antagonist. More specifically, the present invention provides a chemotherapeutic agent effect enhancer having antitumor effects, comprising IL-6 antagonist.

DISCLOSURE OF THE INVENTION

As a result of various studies on the effects of IL-6 antagonist on changes in sensitivity of tumor cells to antitumor agents, the inventors of the present invention found that IL-6 antagonists such as IL-6 antibody or IL-6R antibody increase the sensitivity of tumor cells to antitumor agents, that therapeutic effects are observed with lower doses of antitumor agents, and that therapeutic effects appear by concomitant use of ordinary antitumor agents with an effect enhancer comprising IL-6 antagonist against tumors exhibiting resistance to therapy.

Namely, the present invention relates to a antitumor agent effect enhancer containing IL-6 antagonist. More specifically, the present invention relates to a chemotherapeutic agent effect enhancer having antitumor effects that comprises IL-6 antagonist.

Preferable examples of IL-6 antagonists include antibodies to IL-6 and antibodies to IL-6R such as monoclonal antibodies. Specific examples of monoclonal antibodies include PM-1 antibody and humanized PM-1 antibody. In addition, examples of antitumor agents used in combination with IL-6 antagonists include chemotherapeutic agents such as platinum compounds and mitomycin C having antitumor activity. Examples of platinum compounds include cisplatin, carboplatin, 254-S, DWA-2114R and NK-121.

BRIEF DESCRIPTION OF THE DRAWINGS

FIGS. 1A and 1B indicate the cytotoxicity against renal cell carcinoma line Caki-1 in the presence of cisplatin at a concentration of 0, 0.1, 1 or 10 µg/ml and IL-6 antibody (FIG. 1A) or IL-6R antibody (FIG. 1B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.

FIGS. 5A and 5B indicate the cytotoxicity against renal cell carcinoma line A704 in the presence of cisplatin at a concentration of 0, 0.1, 1 or 10 µg/ml and IL-6 antibody (FIG. 5A) or IL-6R antibody (FIG. 5B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.

FIGS. 6A and 6B indicate the cytotoxicity against fresh renal cell carcinoma obtained from Patient 1 in the presence of cisplatin at a concentration of 0, 0.1, 1 or 10 µg/ml and IL-6 antibody (FIG. 6A) or IL-6R antibody (FIG. 6B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.

FIGS. 7A and 7B indicate the cytotoxicity against fresh renal cell carcinoma obtained from Patient 2 in the presence of cisplatin at a concentration of 0, 0.1, 1 or 10 µg/ml and IL-6 antibody (FIG. 7A) or IL-6R antibody (FIG. 7B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.

FIGS. 8A and 8B indicate the cytotoxicity against fresh renal cell carcinoma obtained from Patient 3 in the presence of cisplatin at a concentration of 0, 0.1, 1 or 10 µg/ml and IL-6 antibody (FIG. 6A) or IL-6R antibody (FIG. 6B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.

FIGS. 9A and 9B indicate the cytotoxicity against renal cell carcinoma line Caki-1 in the presence of carboplatin at a concentration of 0, 1, 10 or 100 µg/ml and IL-6 antibody (FIG. 9A) or IL-6R antibody (FIG. 9B). Diamonds indicate the cytotoxicity (%) in the presence of carboplatin only, squares that in the presence of carboplatin and 0.1 µg/ml IL-6 antibody or IL-6R antibody, triangles that in the presence of carboplatin and 1 µg/ml IL-6 antibody or IL-6R antibody, and circles that in the presence of carboplatin and 10 μg/ml IL-6 antibody or IL-6R antibody.

Figure 10:
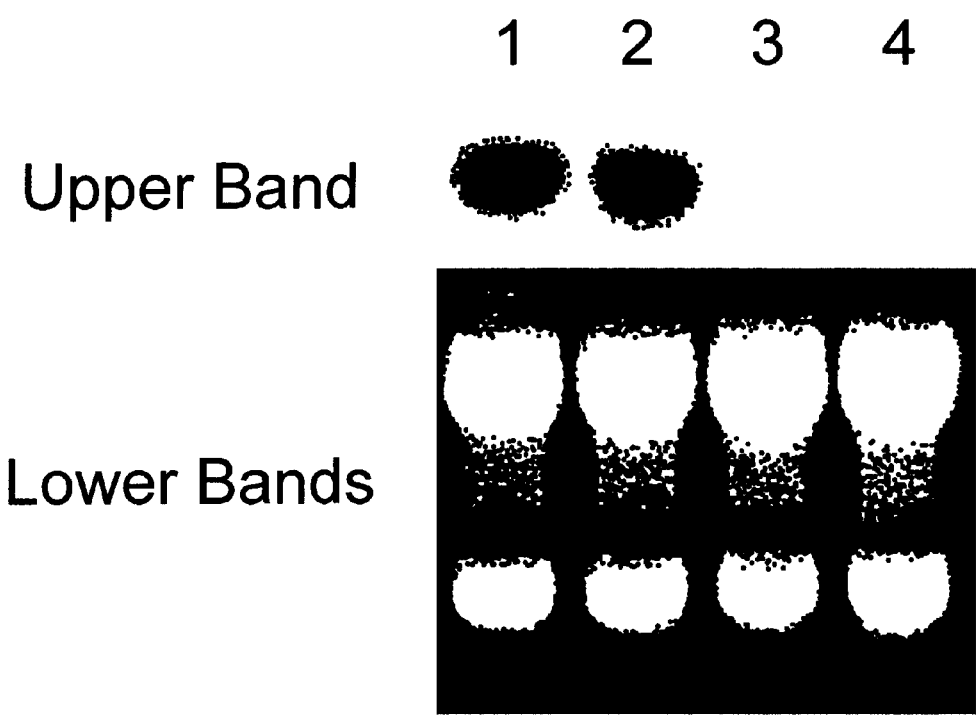

The upper band in FIG. 10 shows the results of Northern blotting of the total RNA of Caki-1 using a GST-π cDNA probe in order to investigate the expression of GST-π mRNA in renal cell carcinoma line Caki-1 treated with a culture medium (control), cisplatin at 10 μg/ml or IL-6 antibody or IL-6R antibody at 10 μg/ml. Lane 1 shows Caki-1 treated with culture medium only, lane 2 that treated with cisplatin, lane 3 that treated with IL-6 antibody, and lane 4 that treated with IL-6R antibody. The two lower bands show the gel used for Northern blotting stained with ethidium bromide. The diagram shows that RNA is present in each lane.

DETAILED DESCRIPTION

The antitumor agent effect enhancer comprising IL-6 antagonist of the present invention enhances antitumor effects by being used in combination with antitumor agents during treatment of tumors. In addition, it enables the required dose of antitumor agent to be decreased since it has the effect of increasing the sensitivity to antitumor agents of therapy-resistant tumors for which therapeutic effects are not observed with ordinary chemotherapy.

Antitumor agents for which antitumor effects are enhanced by the effect enhancer of the present invention are chemotherapy drugs having tumor therapeutic effects that inhibit the development and growth of tumor cells by acting on tumor cells. Examples of chemotherapy drugs include alkylating agents, metabolism antagonists, antitumor antibiotics, alkaloids of plant origin, hormone therapy drugs and platinum compounds. The antitumor antibiotic mitomycin C and platinum compounds having antitumor effects are particularly preferable antitumor agents. Platinum compounds have a platinum atom that forms complexes with other atoms. These compounds exhibit antitumor effects by bonding with DNA, inhibiting DNA synthesis of tumor cells and inhibiting division of tumor cells. Known examples of platinum compounds having antitumor effects that have been used so far include cisplatin (cis-diamine dichloroplatinum (II) having the structural formula shown below):

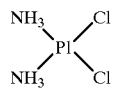

carboplatin (cis-diamine (1,1-cyclobutanedicarboxylato) platinum (II) having the structural formula shown below):

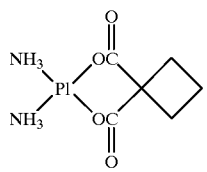

254-S (glycolato-O,O')diamineplatinum (II) having the structural formula shown below:

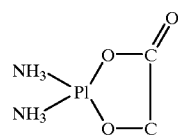

DWA-2114R ((−)-(R)-2-aminomethylpyrrolidine (1,1-cyclobutanedicarboxylatoplatinum (II) having the structural formula shown below):

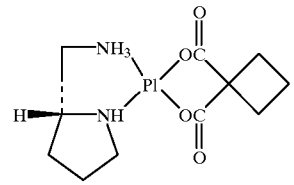

NK-121 ((R)-cis-2-methyl-1,4-butanediamine (1,1-cyclobutanedicarboxylato) platinum (II) having the structural formula shown below:

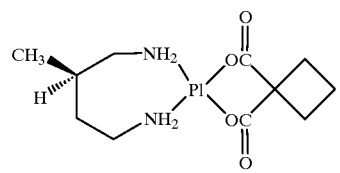

oxsaliplatin (USAN, Oxalato(trans-1,2-cyclohexanediamine) platinum (II) having the structural formula shown below):

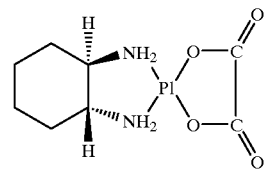

and, TRK-710 ((alpha-acetyl-gamma-methyltetraone)$_2$-(I-1-2-diaminocyclohexane) platinum (II) having the structural formula shown below:

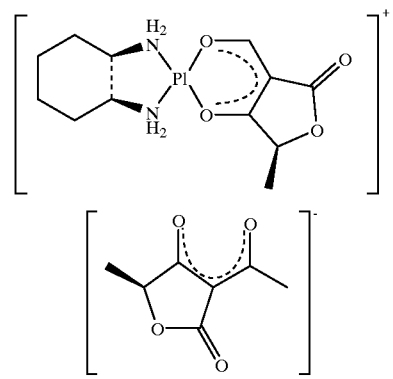

Of these platinum compounds, the above-mentioned cisplatin, carboplatin and DWA-2114R are preferable.

These antitumor agents can be prepared using routine methods. For example, platinum compounds may be used orally or parenterally, and preferably as an injection formulation, by mixing with a pharmaceutical carrier and an excipient, as necessary. For preparing an injective formulation, it may be mixed with distilled water, a salt solution such as sodium chloride or potassium chloride, glucose solution or physiological saline. The amount of antitumor agent in these formulations is preferably a unit dose that is convenient for use according to the patient's age, symptoms and so forth. For example, in using for tumor treatment in an adult, it is daily administered at 10 to 2000 mg/m$^2$ (body surface area), administered continuously for 5 days according to the dose, or a recovery period of 1 to 4 weeks may be provided between administrations.

Tumor cells in which antitumor effects are observed due to the effect enhancer of the present invention are tumors that have IL-6R and exhibit growth and/or resistance to therapy provided by IL-6 as one of their physiologically active substances. Examples of such tumors include renal cell carcinoma (Miki, S. et al., FEBS Letter, 250, 607–610, 1989), myeloma (Kawano, M. et al., Nature, 332, 83–85, 1988), ovarian cancer (Kobayashi, H. et al., Collection of Lecture Abstracts of the 53rd General Meeting of the Japan Cancer Society, p. 271, 874, 1994), B lymphoma of EB virus infection (Tosata, G. et al., J. Virol., 64, 3033–3041, 1990), adult T-cell leukemia (Sawada, T. & Takatsuki, K., Br. J. Cancer Res., 62, 923–924, 1990), prostate cancer (Siegall, C. B. et al., Cancer Res., 50, 7786–7788, 1990), and Kaposi's sarcoma (Miles, S. A. et al., Proc. Natl. Acad. Sci., 87, 4068–4072, 1990).

The IL-6 antagonist used in the present invention may be of any origin provided it blocks signal transmission by IL-6, and inhibits the biological activity of IL-6. Examples of IL-6 antagonists include IL-6 antibody, IL-6R antibody, gp130 antibody, IL-6 mutant, IL-6R antisense oligonucleotide, and partial peptides of IL-6 or IL-6R.

Although there are no limitation on the origin or type (monoclonal or polyclonal) of antibody used as IL-6 antagonist in the present invention, examples of which include IL-6 antibody, IL-6R antibody and gp130 antibody, monoclonal antibody of mammalian origin is particularly preferable. These antibodies inhibit the biological activity of IL-6 by bonding with IL-6, IL-6R or gp130 to inhibit bonding between IL-6 and IL-6R, or between IL-6R and gp130, and blocking signal transmission of IL-6.

There are no particular limitation on the animal species of monoclonal antibody-producing cells provided it is mammalian, and they may originate in human antibody or non-human mammalian antibody. Monoclonal antibodies of rabbit or rodent origin are preferable as monoclonal antibodies of non-human mammalian origin due to the ease of preparation. Although there are no particular limitations on rodent antibodies, preferable examples include mouse, rat and hamster antibodies.

Examples of such IL-6 antibodies include MH166 antibody (Matsuda, et al., Eur. J. Immunol., 18, 951–956, 1988) and SK2 antibody (Sato, et al., 21st General Meeting of the Japan Immunology Society, Scientific Record, 21, 116, 1991). Examples of IL-6R antibodies include PM-1 antibody (Hirata, et al., J. Immunol., 143, 2900–2906, 1989), and AUK12-20, AUK64-7 or AUK146-15 antibody (International Patent Publication No. WO92-19759).

Of these antibodies, IL-6R antibodies are particularly preferable, a specific example of which is the above-mentioned PM-1 antibody.

Monoclonal antibodies can be prepared in the following manner basically using known technology. Namely, using IL-6, IL-6R or gp130 for the sensitizing antigen, a host is immunized in accordance with a routine immunization method, the resulting immunized cells are fused with known parent cells by routine cell fusion, and a monoclonal antibody-producing cell is then selected by routine screening methods.

More specifically, the following procedure may be performed to prepare monoclonal antibody. For example, an antigen of human origin is preferable for the above-mentioned sensitizing antigen, and in the case of human IL-6, antigen is obtained by using the gene sequence of human IL-6 disclosed in Hirano, et al., Nature, 324, 73, 1986. After inserting the gene sequence of human IL-6 into a known expression vector system and transforming suitable host cells, the target IL-6 protein is purified from the host cells or culture supernatant, and the purified IL-6 protein may then be used as the sensitizing antigen.

In the case of human IL-6R, IL-6R protein can be obtained by following a method similar to that of the above-mentioned human IL-6 by using the gene sequence disclosed in European Patent Publication No. EP325474. There are two types of IL-6R, namely that which is expressed on the cell membrane, and a soluble type which is liberated from the cell membrane (sIL-6R) (Yasukawa, et al., J. Biochem., 108, 673–676, 1990). sIL-6R is mainly composed of the extracellular region of IL-6R bonded to the cell membrane, and is different from membrane-bound IL-6R in that it lacks a cell membrane permeating region or cell membrane permeating region and intracellular region.

In the case of gp130, gp130 protein can be obtained by following a method similar to that of the above-mentioned IL-6 by using the gene sequence disclosed in Unexamined European Patent Publication No. EP411946.

Although there are no particular limitations, mammals that are immunized with sensitizing antigen are preferably selected in consideration of compatibility with the parent cells used in cell fusion, and mice, rats, hamsters or rabbits are commonly used.

Immunization of an animal with sensitizing antigen is performed in accordance with known methods. As a typical example, immunization is performed by intraperitoneally or subcutaneously injecting a sensitizing antigen into an animal. More specifically, after diluting and suspending the sensitizing antigen in a suitable amount of phosphate-buffered saline (PBS) or physiological saline, the resulting suspension is mixed with a suitable amount of an ordinary adjuvant, such as Freund's complete adjuvant, as desired followed by emulsification. The emulsion is then preferably administered to the mammal in several doses every 4 to 21 days. In addition, a suitable carrier can also be used during immunization with sensitizing antigen.

Thus, after immunizing the mammal and confirming that the desired antibody level has risen in the serum, the immunized cells are extracted from the mammal and used in cell fusion. A particularly preferable example of immunized cells are spleen cells.

Various known cell lines are preferably used for the mammalian myeloma cells that serve as the parent cells that are fused with the above-mentioned immunized cells, examples of which include P3 (P3x63Ag8.653) (J. Immunol., 123, 1548, 1978), p3-U1 (Current Topics in Microbiology and Immunology, 81, 1–7, 1978), NS-1 (Eur. J. Immunol., 6, 511–519, 1976), MPC-11 (Cell, 8, 405–415, 1976), SP2/0 (Nature, 276, 269–270, 1978), FO (J. Immunol. Meth., 35, 1–21, 1980), S194 (J. Exp. Med., 148, 313–323, 1978), and R210 (Nature, 277, 131–133, 1979).

Cell fusion of the above-mentioned immunized cells and myeloma cells can basically be carried out in accordance with known methods, an example of which is the method of Milstein, et al. (Milstein, et al., Methods Enzymol., 73, 3–46, 1981).

More specifically, the above-mentioned cell fusion is, for example, performed in an ordinary nutrient culture liquid in the presence of cell fusion promoter. Examples of fusion promoters that are used include polyethylene glycol (PEG) and Sendai virus (HVJ). Moreover, a fusion aid such as dimethylsulfoxide can also be added to increase fusion efficiency as desired.

The ratio of immunized cells and myeloma cells used is preferably, for example, 1 to 10 times more immunized cells than myeloma cells. RPMI 1640 culture medium, MEM culture medium or other conventional culture media used in this type of cell culturing can be used for the culture liquid used for the above-mentioned cell fusion. Moreover, these culture media can be used in combination with a serum supplement such as fetal calf serum (FCS).

For cell fusion, prescribed amounts of the above-mentioned immunized cells and myeloma cells are mixed well in the above-mentioned culture medium followed by the addition of PEG solution, such as PEG solution having a mean molecular weight of 1000 to 6000, warmed in advance to about 37° C. normally at a concentration of 30 to 60% (w/v) and mixing to form the target fused cells (hybridoma). Next, by repeating a procedure consisting of sequentially adding a suitable culture medium, centrifuging and removing the supernatant, cell fusion agents and so forth unsuitable for hybridoma growth can be removed.

Said hybridoma is selected by culturing in a conventional selective culture medium such as HAT culture medium (culture medium containing hypoxanthine, aminopterin and thymidine). Culturing in said HAT culture medium is normally continued for several days to several weeks to allow adequate time for cells other than the target hybridoma cells (non-fusion cells) to die. Next, a conventional limited dilution method is performed followed by screening and single-cloning of hybridoma that produces the target antibody.

Hybridoma thus prepared that produces monoclonal antibody can be subcultured in an ordinary culture medium, and can be stored for a long time in liquid nitrogen.

In order to acquire monoclonal antibody from said hybridoma, said hybridoma is cultured in accordance with routine methods, and obtained in the form of culture supernatant. Alternatively, the hybridoma is grown by administering to a mammal with which it has compatibility and obtaining the monoclonal antibody in its ascites. The former method is suited for obtaining highly pure antibody, while the later method is suited for large-volume production of antibody.

In addition, monoclonal antibody can not only be obtained from hybridoma formed by fusing antibody-producing cells obtained by immunizing with antigen, but monoclonal antibody can also be used that is produced using recombinant gene technology by cloning antibody gene, incorporating it in a suitable vector and introducing the vector into a known cell line such as COS or CHO (see, for example, Vandamme, A-M. et al., Eur. J. Biochem., 192, 767–775, 1990).

Moreover, monoclonal antibody obtained by the above-mentioned method can be purified to high purity using routine purification means such as salting out, gel filtration or affinity chromatography.

Monoclonal antibody prepared in this manner is able to recognize antigen with high sensitivity and high accuracy by routine immunological means such as radioimmunoassay (RIA), enzyme immunoassay (EIA, ELISA) and immunofluorescence analysis.

The monoclonal antibody used in the present invention is not limited to monoclonal antibody produced by hybridoma. Monoclonal antibody which has been artificially altered for the purpose of lowering heteroantigenicity to humans and so forth is more preferable. For example, chimeric antibody composed of the variable region of a mammalian monoclonal antibody other than human monoclonal antibody, for example mouse monoclonal antibody, and the constant region of human antibody can be used. This type of chimeric antibody can be produced using known chimeric antibody production methods, and particularly recombinant gene technology.

Moreover, reshaped human antibody can also be used in the present invention. In this type of antibody, the complementarity determining region of non-human mammalian antibody, such as mouse antibody, is grafted to the complementarity determining region of human antibody, by known general gene recombination technique. A reshaped human antibody that is useful in the present invention can be obtained using this known technique, a preferable example of which is reshaped PM-1 antibody (see, for example, International Patent Publication No. WO92-19759).

Furthermore, the amino acids of the framework (FR) region of the variable region of an antibody may be substituted so as that the complementarity determining region of reshaped human antibody forms a suitable antibody binding site (Sato, et al., Cancer Res., 53, 1–6, 1993). Moreover, a gene that code for antibody fragment such as F(ab')$_2$, Fab, Fv, single chain Fv(scFv) linking Fv of H chain and L chain with a suitable linker can be contructed, and the antibody fragment can then be expressed in a suitable host cell and can be used for the above-mentioned purpose provided it binds with antigen and inhibit IL-6 activity (see, for example, Bird, et al., TIBTECH, 9, 132–137, 1991).

An scFv is composed by linking the H chain V region and L chain V region of an antibody. In this scFv, the H chain V region and L chain V region are linked by means of a linker, and preferably by a peptide linker (Huston, J. S. et al., Proc. Natl. Acad. Sci. U.S.A., 85, 5879–5883, 1988). The H chain V region and L chain V region in the scFv may be derived from any of the above-mentioned antibodies. These V regions are preferably linked by a peptide linker. Examples of peptide linkers that are used include any single chain peptide comprising 12 to 19 amino acid residues.

DNA coding for scFv is obtained by using DNA that codes for the H chain or H chain V region of the above-mentioned antibody and DNA coding for the L chain or L chain V region as templates, amplifying the DNA portion of their sequences that codes for the desired amino acid sequence using a primer pair that defines both of its ends, and combining with a primer pair that defines the DNA that codes for the peptide linker portion as well as both ends so as to link with the H chain and the L chain.

In addition, once a DNA coding for scFv has been prepared, an expression vector that contains it and a host transformed by said expression vector can be obtained in accordance with routine methods. In addition, scFv can be obtained in accordance with routine methods by using that host. Since scFv has greater ability to migrate into tissue than antibody molecule, it is expected to be used as substance that has similar functions as reshaped human antibody.

An example of the IL-6 mutant used in the present invention is disclosed in Brakenhoff, et al., J. Biol. Chem., 269, 86–93, 1994 or Savino, et al., EMBO J., 13, 1357–1367, 1994.

IL-6 mutant does not possess the signal transmission effects of IL-6 but retains the bonding activity with IL-6R, and is produced by introducing a mutation in the form of a substitution, deletion or insertion into the amino acid sequence of IL-6. Moreover, as long as the IL-6 from which the IL-6 mutant is derived possesses the above-mentioned properties, there are no limitations on the animal species used. In consideration of antigenicity, however, it is preferable to use that of human origin. More specifically, this is performed by predicting the secondary structure of the amino acid sequence of IL-6 using a known molecular modeling program such as WHATIF (Vriend, et al., J. Mol. Graphics, 8, 52–56, 1990), and then assessing the effect on the overall variant amino acid residues.

After determining suitable amino acid residues to be mutated, a gene that codes for the IL-6 mutant is obtained by introducing a mutation by routinely performed PCR (polymerase chain reaction) while using a vector containing the nucleotide sequence that codes for human IL-6 gene for the template. This can be incorporated into a suitable expression vector as necessary, expressed in E. coli or mammalian cells and either left in the culture supernatant or be isolated and purified in accordance with routine techniques so as to assess binding activity to IL-6R and neutralization of IL-6 signal transmission.

There are no limitations on the sequences of fragments of IL-6 partial peptides or IL-6R partial peptides used in the present invention provided they bond with IL-6 and IL-6R, respectively and do not have the effect of transmitting IL-6 activity. See U.S. Patent Publication U.S. Pat. No. 5,210,075 and Unexamined European Patent Publication No. EP617126 for details regarding IL-6 partial peptides and IL-6R partial peptides. See Japanese Patent Application No. 5-300338 for details regarding IL-6R antisense oligonucleotide.

The antitumor agent effect enhancer comprising IL-6 antagonist of the present invention can be effectively used in the treatment of any tumors having IL-6R, growing by using IL-6 as one of its physiological active substances, and/or exhibiting resistance to therapy, provided it blocks IL-6 signal transmission and assists and enhances the effect of the antitumor agent.

The antitumor agent effect enhancer comprising IL-6 antagonist of the present invention can be administered systemically or locally, and preferably parenterally by, for example, intravenous injection, intramuscular injection, intraperitoneal injection or subcutaneous injection. Moreover, it can be used in the form of a pharmaceutical composition or kit with at least one pharmaceutical carrier or diluent.

The dose in humans of the antitumor agent effect enhancer comprising IL-6 antagonist of the present invention varies according to the condition and age of the patient or according to the administration method. However, it is necessary to select a suitable dose. For example, in the case of IL-6R antibody, a divided dose of four administrations or less within a range of approximately 1 to 1000 mg/patient can be selected. In addition, it can also be administered at a dose of 1 to 10 mg/kg/week. However, the antitumor agent effect enhancer comprising IL-6 antagonist of the present invention is not limited to these doses.

The antitumor agent effect enhancer comprising IL-6 antagonist of the present invention can be prepared in accordance with routine methods (Remington's Pharmaceutical Science, latest edition, Mark Publishing Company, Easton, U.S.A.). For example, preparations for injection may be prepared by dissolving purified IL-6 antagonist in a solvent such as physiological saline, buffer or glucose solution and adding an adsorption prevention agent such as Tween80, gelatin or human serum albumin (HSA). Alternatively, it can also be prepared by freeze-drying for reconstitution prior to use. Examples of vehicles that can be used for freeze-drying include sugar alcohols and sugars such as mannitol and glucose.

EXAMPLES

Although the following provides a detailed explanation of the present invention using examples, reference examples and experiments, the present invention is not limited to them.

Example 1

Effect of IL-6 Antibody or IL-6R Antibody on Sensitivity of Tumor Cells to Antitumor Agents The effect of IL-6 antibody or IL-6R antibody on the sensitivity of tumor cells to various antitumor agents was investigated.

(1) Preparation of Human Renal Cell Carcinoma

Human renal cell carcinoma line Caki-1, cisplatin-resistant strain Caki-1/DDP, a subline of Caki-1, human renal cell carcinoma ACHN and human renal cell carcinoma A704 (Giard, D. J. et al., J. Natl. Cancer Inst., 51, 1417–1423, 1973) were cultured so as to form a single layer in plastic dishes in RPMI 1640 culture medium containing 25 mM HEPES, 2 mM L-glutamine, 1% non-essential amino acids, 100 U/ml penicillin, 100 µg/ml streptomycin and 10% heat-inactivated fetal bovine serum (FBS) (all manufactured by Gibco) (to be referred to as complete culture medium).

On the other hand, fresh tumor cells were obtained from renal cell carcinoma patients in accordance with the method of Mizutani, Y. et al. (Cancer, 69, 537–545, 1992). Renal cell carcinoma tumor tissue was obtained during surgical procedures on three renal cell carcinoma patients. After confirming the tissue to be renal cell carcinoma by histological classification, the tumor tissue was finely decomposed by 3 mg/ml of collagenase (Sigma Chemical Co.) to prepare a tumor cell suspension. After washing three times with RPMI 1640 culture medium, the cell suspension was layered over a non-continuous gradient composed of 2 ml each of 100%, 80% and 50% Ficol-Hypaque in 15 ml volumetric plastic tubes followed by centrifugation for 30 minutes at 400 xg. The lymphocyte-rich monocyte layer contained in the above-mentioned 100% layer was removed, and tumor cells and mesothelial cells were obtained from the 80% layer.

To prevent contamination by other cells, the cell suspension rich in tumor cells was layered over a non-continuous gradient composed of 3 ml each of 25%, 15% and 10% Percoll in complete culture medium contained in 15 ml plastic tubes followed by centrifugation for 7 minutes at 25 xg and room temperature. After washing the resulting tumor cells and suspending in complete culture medium, the presence of tumor cells was confirmed by trypan blue staining. The tumor cells prepared in this manner were used in the following experiment.

(2) Confirmation of IL-6 Production of Renal Cell Carcinoma by ELISA

The presence of IL-6 in the culture supernatant of renal cell carcinoma line Caki-1, Caki-1/DDP, ACHN, A704 and fresh tumor cells derived from renal cell carcinoma patients (Nos. 1–3) was investigated by ELISA (enzyme-linked immunosorbent assay).

100 µl of IL-6 antibody was added to 96-well ELISA plates to coat the ELISA plates with IL-6 antibody by allowing to stand at least overnight. These plates were stored for a maximum of 4 weeks at 4° C. until the time of use. The plates coated with IL-6 antibody were washed three times and blocked for 1 hour with ELISA PBS containing 1% PBS (bovine serum albumin). After washing twice, 100 μl of tumor cell culture supernatant or E. coli recombinant IL-6 as the control (Yasukawa, et al., Biotechnol. Lett., 12, 419, 1990) were added to each well.

The plates were incubated for 1 hour and washed three times followed by the addition of 100 μl of anti-IL-6 polyclonal antibody (Matsuda, T. et al., Eur. J. Immunol., 18, 951–956, 1988) to each well. The plates were then incubated for 1 hour followed by the addition of alkaline phosphate-bound goat anti-rabbit IgG to each well and incubating for an additional hour. The plates were washed and incubated with alkaline phosphate substrate (Sigma 104, Sigma Chemical Co.). Two hours later, the absorbance at 405 nm was measured with an ELISA READER (Immunoreader, Japan Intermed Co., Ltd.). According to those results, the renal cell carcinoma were all clearly shown to produce IL-6 (see Table 1).

TABLE 1

Concentration of IL-6 in Supernatant

| RCC Cells | IL-6 Concentration (pg/ml; mean ± standard deviation |
|---|---|
| Caki-1 | 1337 ± 35 |
| Caki-1/DDP | 3900 ± 325 |
| A704 | 1290 ± 141 |
| ACHN | 1282 ± 106 |
| Fresh RCC cells (Patient No. 1) | 1236 ± 71 |
| Fresh RCC cells (Patient No. 2) | 42 ± 4 |
| Fresh RCC cells (Patient No. 3) | 2579 ± 219 |

(3) Effect of IL-6 Antibody or IL-6R Antibody on the Cytotoxicity of Antitumor agents The MTT method (Mizutani, Y. et al., Cancer, 73, 730–737, 1994) was used to investigate the effect of IL-6 antibody or IL-6R antibody on the sensitivity of various renal cell carcinomas, namely Caki-1, Caki-1/DDP, ACHN, A704 and fresh tumor cells derived from renal cell carcinoma patients (Nos. 1 to 3), to various concentrations of antitumor agents, namely cisplatin (cis-diaminedichloroplatinum (II)), mitomycin C (MMC), adriamycin (ADR), vinblastine (VBL) and 5-fluorouracil (5-FU).

100 μl of the above-mentioned renal cell carcinoma tumor cell suspensions ($2 \times 10^4$ cells) were added to a 96-well bottom-surface microtiter plate (Corning Glass Works, Corning). The plate was incubated in a humid environment at 37° C. in the presence of 5% $CO_2$ and the tumor cells were cultured for 24 hours. The cell culture supernatant was aspirated and the tumor cells were washed three times with RPMI 1640 culture medium. 200 μl of a solution containing each antitumor agent or control in the form of complete culture solution were added to each well in the presence of IL-6 antibody (Matsuda, T. et al., Eur. J. Immunol., 18, 951–956, 1988) or IL-6R antibody (Hirata, Y. et al., J. Immunol., 143, 2900–2906, 1989) followed by culturing for 24 hours at 37° C. 20 μl of MTT solution (5 mg/ml; Sigma Chemical Co.) were added to each well after which culturing was continued for 4 hours in a humid environment at 37° C. and in the presence of 5% $CO_2$. The culture medium was then removed from each well and replaced with isopropanol containing 0.05 N HCl (Sigma Chemical Co.).

The absorbance of the solution in each well at 540 nm was measured with a microculture plate reader (Immunoreader, Japan Intermed Co., Ltd.). The rate of cytotoxicity was calculated with the following formula. Cytotoxicity (%)=[1-(absorbance of experimental group/absorbance of control group)]×100.

Figure 2A:
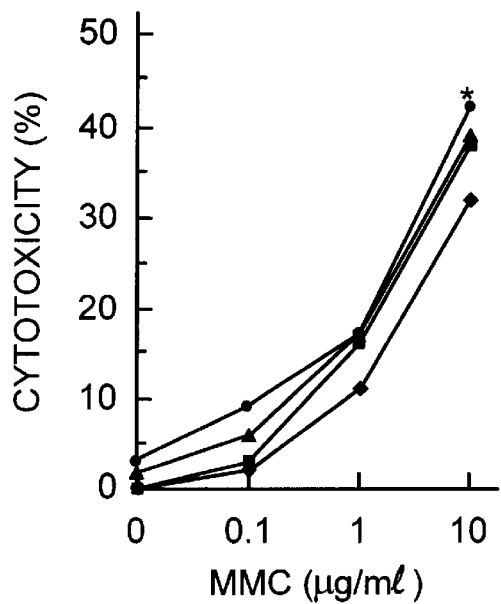
FIGS. 2A and 2B indicate the cytotoxicity against renal cell carcinoma line Caki-1 in the presence of mytomycin C at a concentration of 0, 0.1, 1 or 10 µg/ml and IL-6 antibody (FIG. 2A) or IL-6R antibody (FIG. 2B). Diamonds indicate the cytotoxicity (%) in the presence of mitomycin C only, squares that in the presence of mitomycin C and 0.1 µg/ml IL-6 antibody or IL-6R antibody, triangles that in the presence of mitomycin C and 1 µg/ml IL-6 antibody or IL-6R antibody, and circles that in the presence of mitomycin C and 10 µg/ml IL-6 antibody or IL-6R antibody.
Figure 2B:
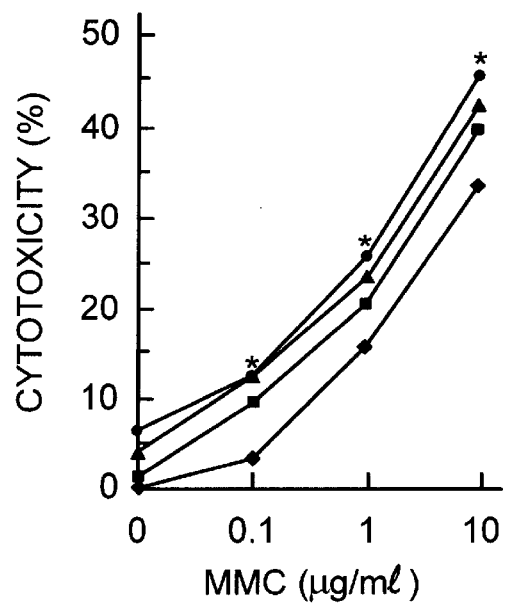

As a result, cytotoxicity caused by cisplatin (see FIGS. 1A and 1B) or MMC (see FIGS. 2A and 2B) in Caki-1 cells clearly increased in the presence of antibody. In the experiment group to which control antibody MOPC3 (J. Natl. Cancer Inst. (Bethesda), 41, 1083, 1968) was added, there were no effects on sensitivity to cisplatin or MMC observed. In comparison with the case of adding antitumor agent alone, the amount of antitumor agent required to elicit cytotoxic effects equivalent to those in the presence of antitumor agent and IL-6 antibody or IL-6R antibody was 1/10 to 1/100. On the other hand, there was no change in the sensitivity of tumor cells to antitumor agents in the presence of IL-6 antibody or IL-6R antibody and ADR, VBL or 5-FU.

Figure 3A:
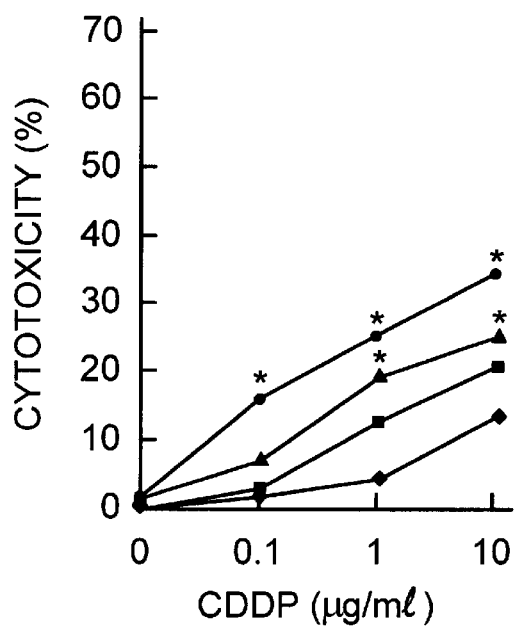
FIGS. 3A and 3B indicate the cytotoxicity against renal cell carcinoma line Caki-1/DDP in the presence of cisplatin at a concentration of 0, 0.1, 1 or 10 µg/ml and IL-6 antibody (FIG. 3A) or IL-6R antibody (FIG. 3B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.
Figure 3B:
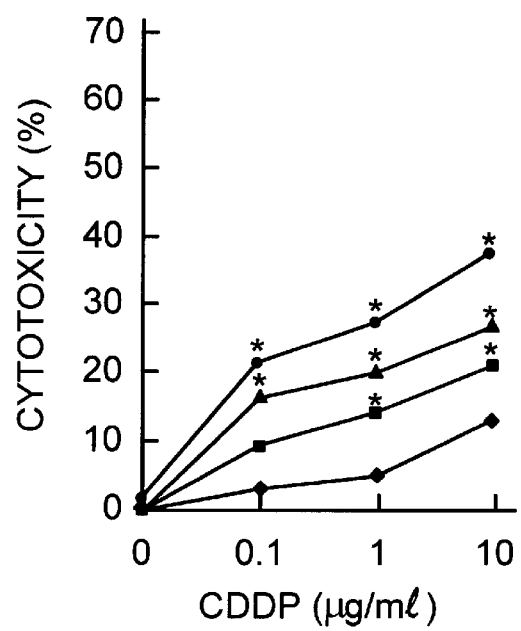
Figure 4A:
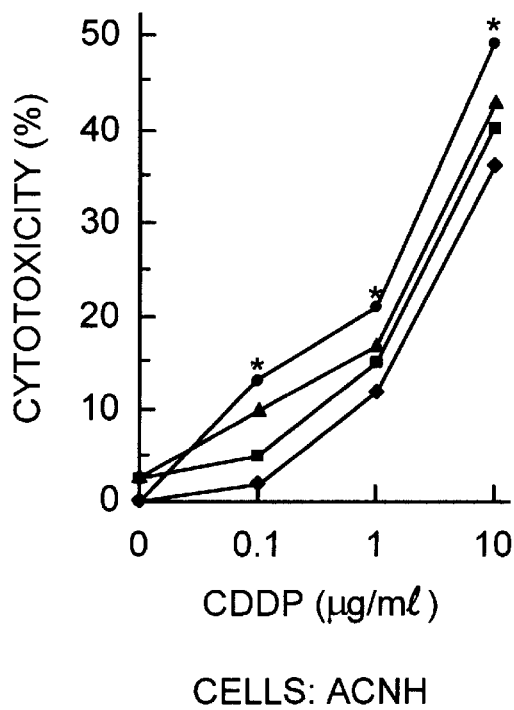
FIGS. 4A and 4B indicate the cytotoxicity against renal cell carcinoma line ACHN in the presence of cisplatin at a concentration of 0, 0.1, 1 or 10 µg/ml and IL-6 antibody (FIG. 4A) or IL-6R antibody (FIG. 4B). Diamonds indicate the cytotoxicity (%) in the presence of cisplatin only, squares that in the presence of cisplatin and 0.1 µg/ml IL-6 antibody or IL-6R antibody, triangles that in the presence of cisplatin and 1 µg/ml IL-6 antibody or IL-6R antibody, and circles that in the presence of cisplatin and 10 µg/ml IL-6 antibody or IL-6R antibody.
Figure 4B:
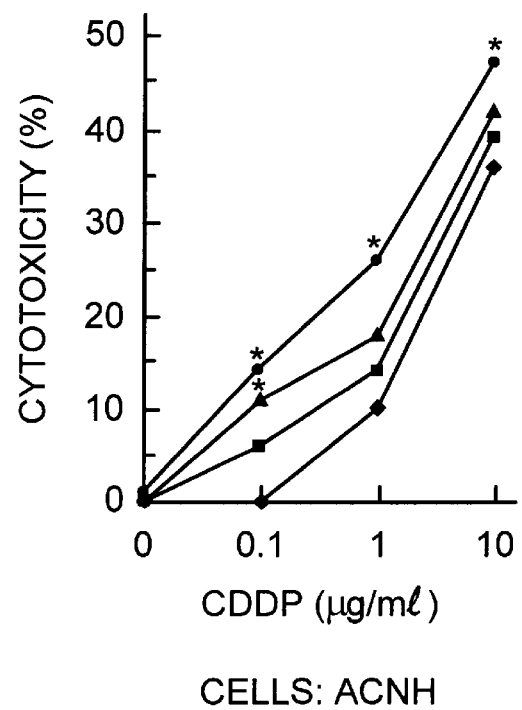

The resistance of Caki-1/DDP cells to cisplatin was overcome by having IL-6 antibody or IL-6R antibody present with the cisplatin (see FIGS. 3A and 3B). The combined effects of IL-6 antibody or IL-6R antibody and cisplatin were similarly observed for the other renal cell carcinoma lines ACHN (see FIGS. 4A and 4B) and A704 (see FIGS. 5A and 5B) as well as for the fresh tumor cells obtained from the three renal cell carcinoma patients (see FIGS. 6A, 6B, 7A, 7B, 8A and 8B).

Example 2

Effect of IL-6 Antibody or IL-6R Antibody on the Sensitivity of Renal Cell Carcinoma to Carboplatin The cytotoxicity when IL-6 antibody or IL-6R antibody was present with carboplatin prepared at various concentrations was examined in the same manner as Example 1 using renal cell carcinoma line Caki-1. As a result, the sensitivity of Caki-1 cells to carboplatin was enhanced (see FIGS. 9A and 9B).

Example 3

Effect of IL-6 Antibody or IL-6R Antibody on Intracellular Accumulation of Antitumor Agents Caki-1 cells were cultured for 24 hours in the presence of combination of 10 μg/ml of cisplatin or 100 μg/ml of 5-FU or culture medium as control, and 10 μg/ml of control antibody MOPC3/C, or 10 μg/ml of IL-6 antibody or IL-6R antibody.

Next, the culture medium was removed and the cells were washed three times with RPMI 1640 culture liquid. The intracellular accumulation of cisplatin was measured by flameless atomic absorption spectrometry (Daley-Tates, P. T. et al., Biochem. Pharmacol., 34, 2263–2369; Riley, C. M. et al., Analytical Biochem., 124, 167–179, 1982). The Zeeman Z-8000 (Zeeman Z-8000 Spectrophotometer, Hitachi Co., Ltd.) was used for the measuring instrument. In addition, the intracellular accumulation of 5-FU was measured by gas chromatography and mass spectrometry (Marunaka, T. et al., J. Pharm. Sci., 69, 1296–1300, 1980). The JMS-D300 mass spectrometer equipped with the JGC-20KP gas chromatograph (JOEL) was used for the measuring instrument. Those results are shown in Table 2. The results clearly showed that IL-6 antibody or IL-6R antibody do not have any effect whatsoever on the accumulation of cisplatin and 5-FU within tumor cells.

TABLE 2

Intracellular Accumulation of CDDP or 5-FU (ng/10$^7$ cells)

| | Treatment | | | |
|---|---|---|---|---|
| Drug | Control (culture medium) | Control Ab | Anti-IL-6 mAb | Anti-IL-6R mAb |
| CDDP | 0.28 ± 0.05 | 0.27 ± 0.02 | 0.26 ± 0.05 | 0.27 ± 0.02 |
| 5-FU | 1.48 ± 0.32 | 1.57 ± 0.45 | 1.50 ± 0.19 | 1.63 ± 0.31 |

Figures in the table were calculated from the data obtained from three experiments (mean±standard deviation).

Example 4

Effect of Cisplatin, IL-6 Antibody or IL-6R Antibody on Expression of Glutathione S-transferase-π (GST-π)

Caki-1 cells were cultured for 4 hours with control culture medium, 10 μg/ml of cisplatin or 10 μg/ml of IL-6 antibody or IL-6R antibody. Next, the total RNA of the cells was prepared according to the method of Mizutani, Y. et al. (Cancer, 73, 730–737, 1994) followed by electrophoresis in 1.2% agarose-2.2 M HCHO gel in 1×MOPS buffer containing 200 mM MOPS (3-[N-morpholino]propane sulfonate), 50 mM sodium acetate and 10 mM sodium EDTA so as to result in 10 μg of RNA per lane. Next, the RNA was transcribed to a Biodyne A membrane (Poll) in 20×SSC solution containing 3 M NaCl and 0.3 M sodium citrate (pH 7.0). A 50 to 100 ng GST-π cDNA probe (Nakagawa, K. et al., J. Biol. Chem., 265, 4296–4301, 1990) was labeled by random oligoprimer elongation using a$^{32}$P-dCTP (NEN). The above-mentioned nylon membrane to which the RNA was transcribed was cross-linked with ultraviolet rays and hybridized with the above-mentioned probe. Those results are shown in FIG. 10.

The expression of GST-π mRNA of Caki-1 cells was not affected at all by cisplatin. However, when IL-6 antibody or IL-6R antibody was added, expression of GST-π mRNA decreased. Based on these findings, it was suggested that the decrease in the level of expression of GST-π mRNA is involved in the increase in sensitivity of renal cell carcinoma to cisplatin caused by IL-6 antibody or IL-6R antibody.

INDUSTRIAL APPLICABILITY

The sensitivity of tumor cells to antitumor agents was observed at lower doses as a result of combining IL-6 antagonists such as IL-6 antibody or IL-6R antibody with antitumor agents, thereby confirming that combined effects are demonstrated by IL-6 antagonists and antitumor agents. Moreover, tumor cells exhibiting resistance to therapy to antitumor agents were proven to be treatable as a result of IL-6 antagonists enhancing their sensitivity to antitumor agents.

In addition, the antitumor agent effect enhancer comprising IL-6 antagonist of the present invention is able to reduce the cytotoxic effects of antitumor agents on tissue by allowing the required dose of antitumor agent to be lowered, thus giving it considerable value in use as an enhancer of antitumor agent effects.

What is claimed is:

1. A kit comprising an antitumor agent, an interleukin-6 (IL-6) antagonist selected from the group consisting of anti-interleukin-6 (anti-IL-6) antibody and anti-interleukin-6 receptor (anti-IL-6R) antibody and a pharmaceutically acceptable carrier or diluent therefor, wherein said antitumor agent and interleukin-6 antagonist are not physically bonded.

2. A method of treating a tumor by inhibiting the development and growth of tumor cells, selected from the group consisting of tumors having an IL-6 receptor, tumors that grow by using IL-6 as a physiologically active substance, and tumors that exhibit resistance to therapy by IL-6 as a physiologically active substance in a subject, said method comprising administering to the subject an interleukin-6 (IL-6) antagonist selected from the group consisting of anti-interleukin-6 (anti-IL-6) antibody and anti-interleukin-6 receptor (anti-IL-6R) antibody in combination with an antitumor agent, wherein said antitumor agent and IL-6 antagonist are not physically bonded, to a patient in need of such treatment, wherein said IL-6 antagonist and antitumor agent are administered in an amount effective to treat said tumor.

3. A method of treating a tumor according to claim 2, wherein the tumor is selected from renal cell carcinoma, myeloma, ovarian cancer, B lymphoma of EB virus infection, adult T-cell leukemia, prostate cancer and Kaposi's sarcoma.

4. A method of treating a tumor according to claim 2, wherein the IL-6 antagonist is a monoclonal antibody.

5. A method of treating a tumor according to claim 4, wherein said monoclonal antibody is PM-1 antibody.

6. A method of treating a tumor according to claim 5, wherein said PM-1 antibody is a humanized PM-1 antibody.

7. A method of treating a tumor according to claim 2, wherein the antitumor agent is a chemotherapeutic drug.

8. A method of treating a tumor according to claim 7, wherein the antitumor agent is selected from the group consisting of cisplatin, carboplatin, 254-S, DWA-2114R and NK-121.

9. A method of treating a tumor according to claim 7, wherein said chemotherapeutic drug is a platinum compound having an antitumor effect.

10. A method of treating a tumor according to claim 7, wherein said chemotherapeutic drug is mitomycin C.

11. A method of treating a tumor according to claim 2, wherein said IL-6 antagonist is human IL-6 antagonist.

12. A method of enhancing a therapeutic effect of an antitumor agent in a subject having a tumor selected from the group consisting of tumors having an IL-6 receptor, tumors that grow by using IL-6 as a physiologically active substance, and tumors that exhibit resistance to therapy by IL-6 as a physiologically active substance in a subject, said method comprising administering to the subject said antitumor agent in combination with an interleukin-6 (IL-6) antagonist selected from the group consisting of anti-interleukin-6 (anti-IL-6) antibody and anti-interleukin-6 receptor (anti-IL-6R) antibody, wherein said antitumor agent and IL-6 antagonist are not physically bonded, and wherein said IL-6 antagonist is administered in an amount effective to enhance the therapeutic effect of the antitumor agent.

13. A method of enhancing the therapeutic effect of an antitumor agent according to claim 12, wherein the IL-6 antagonist is a monoclonal antibody.

14. A method according to claim 13, wherein said monoclonal antibody is PM-1 antibody.

15. A method according to claim 14, wherein said PM-1 antibody is humanized PM-1 antibody.

16. A method of enhancing the therapeutic effect of an antitumor agent according to claim 12, wherein the antitumor agent is a chemotherapeutic drug.

17. A method according to claim 16, wherein said chemotherapeutic drug is a platinum compound having antitumor effects.

18. A method according to claim 16, wherein said chemotherapeutic drug is mitomycin C.

19. A method of enhancing the therapeutic effect of an antitumor agent according to claim 12, wherein the antitumor agent is selected from the group consisting of cisplatin, carboplatin, 254-S, DWA-2114R and NK-121.

20. A method according to claim 12, wherein said IL-6 antagonist is human IL-6 antagonist.

* * * * *